US006167888B1

(12) United States Patent
Tuszynski et al.

(10) Patent No.: US 6,167,888 B1
(45) Date of Patent: Jan. 2, 2001

(54) METHOD FOR INDUCING PARTIAL RECOVERY OF LOST VOLUNTARY MOTOR FUNCTION AFTER SPINAL CORD INJURY IN A MAMMAL

(75) Inventors: Mark H. Tuszynski, La Jolla; Rav Grill, San Diego; Fred H. Gage, La Jolla, all of CA (US)

(73) Assignee: The Regents of the University of California, Oakland, CA (US)

( * ) Notice: Under 35 U.S.C. 154(b), the term of this patent shall be extended for 0 days.

(21) Appl. No.: 09/107,236

(22) Filed: Jun. 30, 1998

Related U.S. Application Data

(60) Provisional application No. 60/051,255, filed on Jun. 30, 1997, now abandoned.

(51) Int. Cl.[7] .................................................. A61B 19/00

(52) U.S. Cl. ........................................... 128/898; 424/570

(58) Field of Search ................................ 424/93.21, 520; 128/898

(56) References Cited

U.S. PATENT DOCUMENTS

| 5,082,670 | * | 1/1992 | Gage et al. | 424/520 |
| 5,529,774 | | 6/1996 | Barba . | |
| 5,676,943 | * | 10/1997 | Baetge et al. | 424/93.21 |

OTHER PUBLICATIONS

Blesch, et al., "Ex Vivo Gene Therapy for Alzheimer's Disease and Spinal Cord Injury," *Clinical Neuroscience*, 3:268–274 (1996).

Davies, A.M., "The neurotrophic hypothesis: where does it stand?" *Philos. Trans. R. Soc. Lond. B. Biol. Sci.*, 351(1338):389–394 (1996).

Farinas, et al., "Severe sensory and sympathetic deficits in mice lacking neurotrophin–3," *Nature*, 369(6482):658–661 (1994).

Furukawa, S., "Neurotrophins as a threapeutic tool for degenerative neuronal disorders," *Rinsho Shinkeigaku*, 33(12):1265–1269 (1993) (Abstract).

Gage, et al., "Gene therapy in the CNS: intracerebral grafting of genetically modified cells," *Prog Brain Res.*, 86:205–217 (1990).

Grill, et al., "Cellular delivery of neurotrophin–3 promotes corticospinal axonal growth and partial functional recovery after spinal cord injury," *The Journal of Neuroscience*, 17(14):1–13 (1997).

Horellou, et al., "Adenovirus–medicated gene transfer to the central nervous system for Parkinson's disease," *Experimental Neurology*, 144(1):131–138 (1997).

Levivier, et al., "Intrastriatal implantation of fibroblasts genetically engineered to produce brain–derived neurotrophic factor prevents degeneration of dopaminergic neurons in a rat model of Parkinson's disease," *Journal of Neuroscience*, 15(12):7810–7820 (1995).

Nakahara, et al., "Grafts of fibroblasts genetically modified to secrete NGF, BDNF, NT–3, or basic FGF elicit differential responses in the adult spinal cord," *Cell Transplant*, 5(2):191–204 (1996).

Raymon, et al., "Application of ex Vivo gene therapy in the treatment of Parkinson's disease," *Experimental Neurology*, 144(1):82–91 (1997).

Schecterson, et al., "Novel roles for neurotrophins are suggested by BDNF and NT–3 mRNA expression in developing neurons," *Neuron.*, 9(3):449–463 (1992).

(List continued on next page.)

*Primary Examiner*—David J. Isabella
*Assistant Examiner*—Kelly O'Hara
(74) *Attorney, Agent, or Firm*—Foley & Lardner

(57) ABSTRACT

The invention provides means for inducing partial recovery of motor function lost in a mammal as a consequence of an injury to its spinal cord which includes a lesion of the cerebrospinal projections (CST) of the cord. Axonal growth is initiated in the CST, and functional recovery obtained, by delivering neurotrophin-3 to the site of CST injury by expression from a recombinant expression vector.

11 Claims, 12 Drawing Sheets

OTHER PUBLICATIONS

Schinstine, et al., "Intracerebral delivery of growth factors: potential application of genetically modified fibroblasts," *Prog. Growth Factor Res.*, 3(1):57–66 (1991).

Schnell, et al., "Neurotrophin–3 enhances sprouting of corticospinal tract during development and after adult spinal cord lesion," *Nature*, 367(6459):170–173 (1994).

Senut, et al., "Regional differences in responsiveness of adult CNS axons to grafts of cells expressing human neurotrophin 3," *Exp. Neurol.*, 135(1):36–55 (1995).

Shvaloff, et al., "Lines of therapeutics research in Alzheimer's disease," *Psychopharmacology Bulletin*, 32(3):343–352 (1996).

Tuszynski, et al., "Central infusions of brain–derived neurotrophic factor and neurotrophin–4/5, but not nerve growth factor and neurotrophin 3, preent loss of the cholinergic phenotype in injured adult motor neurons," *Neuroscience*, 71(3):761–771 (1996).

Tuzsynski, et al., "Fibroblasts genetically modified to produce nerve growth factor induce robust neuritis ingrowth after grafting to the spinal cord," *Exp. Neurol.*, 126(1):1–14 (1994).

Tuzsynski, et al., "Functional characterization of NGF–secreting cell grafts to the acutely injured spinal cord," *Cell Transplant*, 6(3):361–368 (1997).

Tuzsynski, et al., "Gene therapy in the adult primate brain: intraparenchymal grafts of cells genetically modified to produce nerve growth factor prevent cholinergic neuronal degeneration," *Gene Therapy*, 3:305–314 (1996).

Tuzsynski, et al., "Nerve growth factor delivery by gene transfer induces differential outgrowth of sensory, motor, and noradrenergic neurites after adult spinal cord injury," *Exp. Neurol.*, 137(1):157–173 (1996).

Tuszynski, et al., "Neurotrophic factors and diseases of the nervous system," *Ann. Neurol*, 35 Suppl:S9–S12 (1994).

Tuszynski, et al., "Recombinant human nerve growth factor infusions prevent cholinergic neuronal degeneration in the adult primate brain," *Ann. Neurol*, 30(5):625–636 (1991).

Tuzsynski, et al., "Somatic gene therapy for nervous system disease," *Ciba Found Symp*, 196:85–94 (1996).

Tuzsynski, et al., "Somatic gene transfer to the adult primate central nervous system: in vitro and in vivo characterization of cells genetically modified to secrete nerve growth factor," *Neurobiol. Dis.*, 1(1–2):67–78 (1994).

Yang, et al., "DC–Chol liposome–mediated gene transfer in rat spinal cord," *Neuroreport*, 8(9–10):2355–2358 (1997).

Yang, et al., "Gene therapy for central nervous system injury: the use of cationic liposomes: an invited review," *J. Neurotrauma*, 14(5):281–297 (1997).

Zhou, et al., "Peripheral projections of rat primary sensory neurons immunoractive for neurotrophin 3," *J Comp Neurol*, 363(1):69–77 (1995).

Zlokovic, et al., "Cellular and molecular neurosurgery: pathways from concept to reality—part I: target disorders and concept approaches to gene therapy of the cental nervous system," *Neurosurgery*, 40(4):789–803 (1997).

Zlokovic, et al., "Cellular and molecular neurosurgery: pathways from concept to reality—part II: vector systems and delivery methodologies for gene therapy of the central nervous system," *Neurosurgery*, 40(4):805–812 (1997).

Diikhuizen, et al., "Characterization of an adenoviral vector encoding NT–3 and its application in neuroregeneration research," *Society for Neuroscience*, 23:53 (1997).

Conner, et al., "Distribution of NGF delivered into the rat CNS by either grafted NGF–secreting fibroblasts, intraparenchymal (IP) injections, or IP–infusions," *Society for Neuroscience*, 23:53 (1997).

Goins, et al., "Herpes simplex virus (HSV) vector–mediated nerve growth factor (NGF) expression in models of neurodegenerative disease," *Society for Neuroscience*, 23:53 (1997).

Staecker, et al., "BDNF gene therapy in the inner ear prevents loss of spiral ganglion neurons," *Society for Neuroscience*, 23:53 (1997).

Blömer, et al., "Lentiviral transfer of NGF and BCL–xL rescues axotomized cholinergic neurons in vivo," *Society for Neuroscience*, 23:53 (1997).

Baumgartner, et al., "Neuroprotection of spinal motoneurons with adenoviral vectors containing neurotrophic factor genes," *Society for Neuroscience*, 23:53 (1997).

Tuszynski, et al., "The chronically injured spinal cord exhibits responsiveness to NGF delivered locally by gene therapy," *Society for Neuroscience*, 21:1562 (1995).

Wiegand, et al., "Effects of BDNF infusion on locomotor behavior and dopamine neurite outgrowth from fetal mesencephalic transplants," *Society for Neuroscience*, 21:1562 (1995).

Date, et al., "Transplantation of polymer–encapsulated human NGF–secreting cells promotes chromaffin cell survival and behavioral recovery in hemiparkinsonian rats," *Society for Neuroscience*, 21:1562 (1995).

Roberts, et al., "Effects of NGF–secreting genetically modified cell grafts on cholinergic neuronal morphology and cognition in aged primates," *Society for Neuroscience*, 21:1562 (1995).

\* cited by examiner 1 gagctcaaac atagggagat aagtgctgtt ttcacaagat aaaggcaaaa ttcaatccca
     61 cgttgccgtt ttgtttctgt tcagtgttcc aaccacagag tggtgctatt gcaaaagata
    121 agggtaacca gaaggcacga tctggaaatt tgctttagga gagagtttta aaggggttt
    181 tcaaaaacaa gatctgattc ctgctctcag aaatcacttc caggagtcag ggccttactc
    241 tcagatgcag cagggagaag aagaaagttc agcaacctaa aaatacagtc gacagatggg
    301 cagccaaagt catggccacg aagtcaactt ggagaggagc acctacctag tgaatcctaa
    361 aagatctcat cctggatgct tccttaacca ggcctatgta cagggcacaa gctcgcagcc
    421 agcttacttt ccagtcctga tctttgcttt tgctatccat accaatggta tttctataga
    481 aaagaaaaat ctctatttag aaacacggat ttacttagaa gtcacaatat tctagtttaa
    541 aaatggctct acatagtaga gaatgatctt tttattctgt cttcttaaaa atacaccttt
    601 ctaattcttt ttttcttccc accttcttca ttcagcacct tgccactccc ttggaagcca
    661 caacagcgag ctggggggtc agtccctagt cttagaggga agaaatcttt aggtctgaag
    721 tctaaagaaa aacagtaaag gaaaggcag ttggcggtgc tcaaggtaga ctgtctgaaa
    781 gaggtcttct actcagaaaa gggctaaggc tctccctttg ggaaaccaat ccttctgaga

Fig. 5A

```
 841 aaaagtgcat ctttcaccct ctgctcctgt ctgggtctct ccctcttcct
ccctccttcc
 901 ctcagtccct cctcccctct ctccacaaag acacagcaca tatttggcaa
gattaaggtg
 961 tcacctctca tattacaagg cctgttgatt gcaagcaaag acagacccac
cagcttagga
1021 caaaacccct tggagttgga aataagacaa actctgggat ccccgaaagt
cccggcaaaa
1081 tgacgcggcc agccagtgca aggcatctgc agaacaaatc caagtcctaa
acgcactgct
1141 tgctgccttt tcttctcctt cctttcttct gatttttcaa gtttgtttgc
ccccttccc
1201 ctcctccctc cagactgcca gggacctggg agctgcctgc agatcagccc
gcacatgtat
1261 ttaacccctt ccctgctgca gcaggagcca accacctctt tccttgcaat
cttcaggttc
1321 ccagaggacc tggagcttga gaaaagaact ctgccagtgg atctgaaact
ggggcctgaa
1381 tccctccttt gaccagggcg agaagctgga ggagggggc aagtgcggga
agtgggggag
1441 ggcagggagg cgggccagat gagagggaga aaagcagaac ccgacagagc
acgcccaatc
1501 caaaccttca tggtgctgtg tggctgggtg gagggaacga ctcggcagcc
tcttctggcc
1561 ctgaggaaga cgtcgatatt ttggcacgag gggagccact gaaggactac
cctacccttg
```

Fig. 5B

```
1621 cgagggaccg caggaggtga cgcccctggg cctcggtggg cgcttctggc
ggttttcgat
1681 gtggcaaccc ccatcagcca ggataatgat gaggcaggta caatctatct
agtacgcagc
1741 ccccagactc cccctccct tcccacctcc ccatccaacc ccccagctac
tctctgcggc
1801 cggttggtcc tgaactggtg ggtgcagttc cgatgtttaa ccaaattctc
aagcaatttc
1861 aaggtatttg gattttttga acctgggccc taaccgaaac gcggaacggc
ttgcttatta
1921 gacacctcga acgacagcgc agggaggaaa cgggatactc gctgcccttc
ccagtcgcgc
1981 gtgagtcaaa aggtcctggc aggagatgat gtgaggagcg gctgaagtgg
cagggagcaa
2041 gggatgaggg gcttggagcg gaggtccacc acgcaaggac tcgggaagcg
ggcaagtggg
2101 caaaactctg cttccgggct ctcgatttct cgttgatcac taagtggtat
ttttccccct
2161 tctctcgatg gcaaatgggc gaaatcaaga tgacttaact tggtaaattt
agagagaac
2221 gctcggagca agtgaggtct aacgggcagc taaaattatc tccaaataag
agattttgac
2281 cccctccccc tatcctctcc tcgaatgtat ccaccggtgg ggaagtgagc
gtcattactt
2341 tcggggcgcc acgacaggtt tgtttgttgc tcgcctttcc tgcttctcgc
gctgtccccg
2401 cgtgcagact ggtgggtgct gggcgagtga ttagctgcag ggccccatcc
tagtttggaa
```

Fig. 5C

```
2461 ggaaggggtt tagaagttgg aggatgggtg aaatgggagg ctgcgatcca
tctccctctc
2521 ccttccacac tcaagctccc gcaaacacgc gcgcgcacac acagcccctc
cctagtccct
2581 cggaccaccc gccccacgc cctctacct tgacctccct tgaccgccga
cacagcgtcc
2641 tgggtgcggg tccccgggag cggggagttc gccggggagc gattgtcctt
gggcgtgttc
2701 gtgctgtggg gtgggggag gagtggcggg tgggcttggt aggggtggg
gagagatctg
2761 gagctggaag ggtctaaggt ttggaggagg agtttacccc tcagacctga
tcctcctgac
2821 caaaaaggca ggaaaaggcc ctgatgcctt gtaaagaaaa tcttgaaaga
aaaaagatca
2881 aaaagaaaaa tttcaagaaa aagaaccact aagaaaggct gaagacacta
acatgtaacc
2941 tgttacgata catttaacgt ttcgtttttt cctggatctc taaaagggaa
ctcaagggtg
3001 ggggttactg aagaatacta cagatttgga agttttgtt gctgttgttg
tttggtttgg
3061 ttttgttttt caagaggggc caggagaaat gaccccttcc ccgccacggg
tcccgaagtg
3121 agggcggggg gggggctctg gggcgcgggc gcgcgcggcg cggcgcgggc
cggcgggga
3181 gggcggcgcg gcgcggaagg ggttaaggcg ctgagcgcgg agccatctgg
ccgggttggc
```

Fig. 5D

```
3241 tggttataac cgcgcagatt ctgttcacgg gactcagagt tgaagctcct
ctcccttccg
3301 aacacgtccg cgcaccgccc cgcgacgcag cccggcgcaa ctactttctt
ctctctcctt
3361 tctttcttcc tctccttttt ccctgctgg gtagtggctg cggcggggtg
ggggagactt
3421 tgaatgaccg agctcgcgtc cacctttctc ttcatgtcga cgtccctgga
aacggccaca
3481 cggatgccat ggttactttt gccacggtaa ggggaggcgg cgggcacctt
gggtgggcag
3541 gtttggggat ggggtccac gtggggaggg attttccagt ggactggtgc
gggggccccc
3601 agatccgcat cccgccccac ccccatcgcg ccgcgctcac tcactttccc
gggcttgtgt
3661 cttccccaaa gtttgcgctg ggatctgctc aggccgaagc gcaaccgcag
ccaccccgct
3721 acacacacac acacacacac acacacacac acacacacac acagacacgg
acaccttct
3781 ccacctcctc ccctcttgtc cctcggctgc ccaagaagct t
```

Fig. 5E

```
  1 agagagcgct gggagccgga ggggagcgca gcgagttttg gccagtggtc gtgcagtcca
 61 aggggctgga tggcatgctg gacccaagct cagctcagcg tccggaccca ataacagttt
121 taccaaggga gcagctttct atcctggcca cactgaggtg catagcgtaa tgtccatgtt
181 gttctacact ctgatcacag cttttctgat cggcatacag gcggaaccac actcagagag
241 caatgtccct gcaggacaca ccatccccca agtccactgg actaaacttc agcattccct
301 tgacactgcc cttcgcagag cccgcagcgc cccggcagcg gcgatagctg cacgcgtggc
361 ggggcagacc cgcaacatta ctgtggaccc caggctgttt aaaaagcggc gactccgttc
421 accccgtgtg ctgtttagca cccagcctcc ccgtgaagct gcagacactc aggatctgga
481 cttcgaggtc ggtggtgctg ccccttcaa caggactcac aggagcaagc ggtcatcatc
541 ccatcccatc ttccacaggg gcgaattctc ggtgtgtgac agtgtcagcg tgtgggttgg
601 ggataagacc accgccacag acatcaaggg caaggaggtg atggtgttgg gagaggtgaa
```

Fig. 6A

```
661 cattaacaac agtgtattca aacagtactt ttttgagacc aagtgccggg acccaaatcc
721 cgttgacagc gggtgccggg gcattgactc aaagcactgg aactcatatt gtaccacgac
781 tcacaccttt gtcaaggcgc tgaccatgga tggcaagcag gctgcctggc ggtttatccg
841 gatagatacg gcctgtgtgt gtgtgctcag caggaaggct gtgagaagag cctgacctgc
901 cgacacgctc cctcccctg ccccttctac actctcctgg gccctccct acctcaacct
961 gtaaattatt ttaaattata aggactgcat ggtaatttat agtttataca gttttaaaga
1021 atcattattt attaaatttt tggaagc
```

Fig. 6B

METHOD FOR INDUCING PARTIAL RECOVERY OF LOST VOLUNTARY MOTOR FUNCTION AFTER SPINAL CORD INJURY IN A MAMMAL

This application claim benefit to Provisional Application 60/051,255 Jun. 30, 1997 now abandoned.

STATEMENT CONCERNING FEDERALLY FUNDED RESEARCH

The work described in this disclosure was funded by a VA Merit RVW Grant from the United States Veterans Administration. The Government may have certain rights to this invention.

BACKGROUND FOR THE INVENTION

1. Field of the Invention

The invention relates to methods for treating spinal cord injuries in a mammal. Specifically, the invention relates to a method for inducing partial recovery of voluntary motor function in a mammal after disruption of corticospinal projections in the spinal cord.

2. History of the Art

The mammalian spinal cord shows little spontaneous recovery after injury. Furthermore, although regeneration of damaged spinal cord tissues (e.g., axons and neurons) can sometimes be induced through treatment, the treated animals still do not usually recover whatever voluntary motor function was lost to the injury.

The degree of motor function loss varies with the identity of the damaged tissue and the extent of damage incurred, as well as with species. For example, the rubrospinal tract influences movement through direct and reciprocal spinal motor projections that reflect activity of the rubro-cortico-cerebellar premotor pathway. The vestibulospinal and reticulospinal tracts affect postural control and balance during locomotion. Specialization in the vestibular system in particular has been important for the evolution of bipedal locomotion in humans. However, impairments in voluntary motor function after spinal cord injury in humans are most often attributed to disruption of corticospinal tract (CST) projections.

In rats, a species frequently used to study spinal cord regeneration, CST lesions have been reported to impair skilled motor movements, such as reaching, preferred limb use, and "placing" responses (reflex limb withdrawal to touch). Studies in cats and non-human primates report that the CST is involved in voluntary modification of gait, inducing alterations in amplitude, duration and temporal patterns of muscle activity during locomotion through both direct projections to motor neurons and through modification of activity of spinal cord pattern generators. In humans, some voluntary motor function can occasionally be recovered spontaneously despite isolated lesions of the CST, although function is generally inferior to the prelesioned state.

Two reports of partial functional recovery resulting from regrowth of host projections after spinal cord injury have recently been published. In one approach, CNS myelin-associated growth inhibitors were neutralized (Bregman B S, Kunkel-Bagden E, Schnell L, Dai H N, Gao D, Schwab M E (1995) Recovery from spinal cord injury by antibodies to neurite growth inhibitors. Nature 378:498–501), resulting in regrowth of axons through host white matter. In a second study, delivery of acidic fibroblast growth factor reportedly generated growth responses from all supraspinal systems studied, resulting in some functional recovery after complete spinal cord transections (Cheng H, Yihai C, Olson L. (1996) Spinal cord repair in adult paraplegic rats: Partial restoration of hind limb function. Science 273:510–513). Regenerating axons in the latter experiment were specifically directed toward host gray matter to avoid myelin-based inhibitors. These findings highlight the importance of defining appropriate growth terrains for injured adult CNS axons and of identifying specific growth-promoting neurotrophic factors.

SUMMARY OF THE INVENTION

The invention provides a method for treating a mammal which has suffered an injury to its spinal cord involving the CST and has lost some voluntary sensorimotor function as a consequence of the injury. Uninjured spinal cord tissue is not affected by the inventive treatment method. According to the method, a CST neurotrophin (such as NT-3) is delivered to the mammal to act on the spinal cord at the site of the CST lesion. Practice of the method of the invention not only produces regrowth of CST projections in the presence of gray matter tissue, but also surprisingly results in the restoration of a degree of the lost voluntary motor function.

Specifically, consistent with expectations, animals treated according to the invention undergo some growth of CST axonal projections at the site of a spinal cord injury. However, in stark contrast to prior experience with many treatments for spinal cord injuries, the treated animals also recovered some motor function whose loss was attributable to the CST injuries inflicted on each animal prior to treatment. Interestingly, voluntary motor function is restorable through use of the method of the invention to treat CST lesions in animals whose spinal cord injuries extend beyond the CST.

Exposure of the lesions to CST neurotrophin can be prolonged for a time sufficient to induce functional recovery (as compared to, for example, single dosing with NT-3) by grafting syngenic cells which have been engineered to express CST neurotrophin to the site of the CST lesions in the presence of an appropriate growth substrate (i.e., host gray matter). Another method for delivery of the CST neurotrophin to CST lesions supplies an CST neurotrophin coding recombinant expression vector into the lesioned spinal cord.

Treatment of CST lesions according to the invention may be supplemented by any treatment or therapy appropriate to the nature and degree of injury in the affected mammal.

BRIEF DESCRIPTION OF DRAWINGS

FIG. 1 (a through c): Functional effects of spinal cord lesions.

FIG. 5: A nucleotide sequence coding for human βNGF neurotrophin (SEQ.ID.No. 1).

FIG. 6: A nucleotide sequence coding for human NT-3 neurotrophin (SEQ.ID.No. 2).

DETAILED DESCRIPTION OF THE PREFERRED EMBODIMENTS

A. Goal of Inventive Method

Figure 1A:
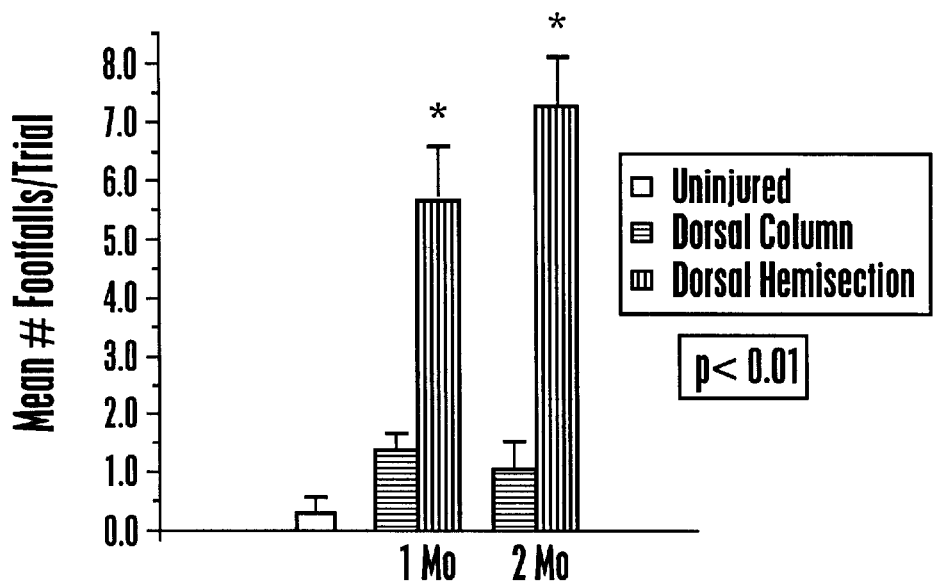
FIG. 1a: Grid task: Rats with dorsal hemisection lesions but not dorsal column lesions show persistent functional deficits reflected by a significant increase in the number of footfalls (Anova $p<0.01$).

As demonstrated in the data described in Example II, CST trauma is apparently not solely responsible for the all losses of voluntary sensorimotor function which can occur in animals suffering from spinal cord injuries. Rather, damage to other dorsal spinal projections as well as ventral regions of the spinal cord also produces varying degrees of motor impairment. Nonetheless, the severity of functional deficit experienced by an animal is significantly exacerbated by dorsal or ventral CST damage. Therefore, amelioration of CST damage according to the invention reduces the severity of such deficits by restoring partial motor function associated with normal CST activity.

To that end, animals are treated with recombinant CST neurotrophin over a course of treatment which preferably provides continuous delivery of CST neurotrophin to lesioned CST sites over a course of several weeks or months. As shown in Example II, animals so treated for three months with the neurotrophin NT-3 experienced induced growth of corticospinal axons both at and caudal to the site of an inflicted spinal cord injury.

B. Preparation of CST Neurotrophin Encoding Expression Vectors and Delivery of CST Neurotrophin According to the Invention 1. CST Neurotrophins One particularly effective method of extended delivery provides CST neurotrophin secreted continuously by genetically modified cells grafted to the injured spinal cord. To this end, cells such as fibroblasts are tranfected ex vivo with a recombinant expression vector engineered to express and secrete: CST neurotrophin or a recombinant expression vector is constructed to express the CST neurotrophin and delivered directly into the region of damaged cells.

Known neurotrophins include a primary nerve growth factor (NGF), brain-derived neurotrophic factor (BDNF), neurotrophin 3 (NT3), neurotrophin 4/5 (NT-4/5), neurotrophin 6 (NT-6), ciliary neurotrophic factor (CNTF), glial cell line-derived neurotrophic factor (GDNF), fibroblast growth factor 2 (FGF-2), leukaemia inhibitory factor (LIF) and certain members of the insulin-like growth factor family (e.g., IGF-1). Those of ordinary skill in the art will be familiar with, or can readily ascertain, the identity of neurotrophins which stimulate growth of CNS cells, especially CST projections in adults, such neurotrophins are collectively referred to herein as "CST neurotrophins". NGF and NT3 in particular have been tested with promising results in clinical trials and animal studies (see, e.g., Hefti and Weiner, *Ann Neurol.*, 20:275–281 (1986); Tuszynki and Gage, *Ann. Neurol.*, 30:625–636 (1991); Tuszynski, et al., *Gene Therapy*, 3:305–314 (1996) and Blesch and Tuszynski, *Clin. Neurosci.*, 3:268–274 (1996)). For this reason, of the known neurotrophins, βNGF and NT-3 are preferred for use in the invention.

Human (h) βNGF and hNT3 are preferred for use in therapy of human CNS impairment according to the invention due to their relatively low immunogenicity as compared to allogenic growth factors. However, other nerve growth factors are known which may also be suitable for use in the invention with adequate testing of the kind described herein.

Coding polynucleotides for hβNGF and hNT3 are known, as are coding sequences for neurotrophins of other mammalian species (e.g., mouse, in which the coding sequence for βNGF is highly homologous to the human coding sequence). For example, a cDNA including the coding sequence for hβNGF is reported in GENBANK at E03015 (Kazuo, et al, Japanese Patent Application No. JP19911175976-A, while the nucleotide sequence of genomic βNGF (with putative amino acid sequence) is reported in GENBANK at HSBNGF (Ullrich, *Nature*, 303:821–825 (1983)) and the mRNA sequence is reported in GENBANK at HSBNGFAC (Borsani, et al., *Nucleic Acids Res.*, 18:4020 (1990)). The genomic nucleotide sequence of hNT3 is reported in GENBANK at E07844 (Asae, et al., JP Patent Application No. 1993189770-A4). These references are incorporated herein to illustrate knowledge in the art concerning nucleotide and amino acid sequences for use in synthesis of neurotrophins. Exemplary reprints of nucleotide sequences coding for βNGF and NT3 obtained from the GENBANK nucleotide database are provided in, respectively, FIGS. 5 and 6.

2. Donor Cells for Grafting and Construction of Recombinant Expression Vectors Coding for CST Neurotrophins A preferred method for preparation of donor cells containing a nerve growth factor transgene encoding expression vector is described in detail in commonly assigned U.S. Pat. No. 5,650,148, the contents of which are incorporated herein. The preparation is carried out by modifying donor cells such as fibroblasts by introduction of a retroviral vector containing a transgene or transgenes encoding a CST neurotrophin.

For convenience, the discussion below will focus on delivery of NT-3 as the CST neurotrophin of the invention. However, those of ordinary skill in the art will recognize that the methods described are adaptable to construction of donor cells for use in delivery of transgenes encoding other CST neurotrophins.

The strategy for transferring genes into donor cells in vitro includes the following basic steps: (1) selection of an appropriate transgene or transgenes whose expression is correlated with CNS disease or dysfunction; (2) selection and development of suitable and efficient vectors for gene transfer; (3) preparation of donor cells from primary cultures or from established cell lines; (4) demonstration that the donor implanted cells expressing the new function are viable and can express the transgene products(s) stably and efficiently; (5) demonstration that the transplantation causes no serious deleterious effects; and (6) demonstration of a desired phenotypic effect in the host animal.

The methods described below to modify donor cells using retroviral vectors and grafting into the CNS are merely for purposes of illustration and are typical of those that might be used. However, other procedures may also be employed, as is understood in the art. In particular, most of the techniques used to transform cells, construct vectors and the like are widely practiced in the art, and most practitioners are familiar with the standard resource materials which describe specific conditions and procedures. However, for convenience, the following paragraphs may serve as a useful guideline.

i. Choice of donor cells

The choice of donor cells for implantation depends heavily on the nature of the expressed gene, characteristics of the vector and the desired phenotypic result. Because retroviral vectors require cell division and DNA synthesis for efficient infection, integration and gene expression (Weiss et al., *RNA Tumor viruses,* 2nd Ed., Weiss et al., eds., Cold Spring Harbor Press, N.Y. (1985)), if such vectors are used, the donor cells are preferably actively growing cells such as primary fibroblast culture or established cell lines, replicating embryonic neuronal cells or replicating adult neuronal cells from selected areas such as the olfactory mucosa and possibly developing or reactive glia. Primary cells, i.e. cells that have been freshly obtained from a subject, such as fibroblasts, that are not in the transformed state are preferred for use in the present invention. Other suitable donor cells include immortalized (transformed cells that continue to divide) fibroblasts, glial cells, adrenal cells, hippocampal cells, keratinocytes, hepatocytes, connective tissue cells, ependymal cells, bone marrow cells, stem cells, leukocytes, chromaffin cells and other mammalian cells susceptible to genetic manipulation and grafting using the methods of the present invention. Species-matched cells are preferred; e.g., primate cells for delivery to primates, human cells for delivery to humans and so forth.

The application of methods to induce a state of susceptibility in stationary, non-replicating target cells may make many other cell types suitable targets for viral transduction. For instance, methods have been developed that permit the successful retroviral vector infection of primary cultures of adult rat hepatocytes, ordinarily refractory to infection with such vectors, and similar methods may be helpful for a number of other cells (Wolff et al., *Proc. Natl. Acad. Sci. USA* 84:3344–3348 (1987)). In addition, the development of many other kinds of vectors derived from herpes, vaccinia, adenovirus, or other viruses, as well as the use of efficient non-viral methods for introducing DNA into donor cells such as electroporation (Toneguzzo et al., *Molec. Cell. Biol.* 6:703–706 (196)), lipofection or direct gene insertion may be used for gene transfer into many other cells presently not susceptible to retroviral vector infection.

Additional characteristics of donor cells which are relevant to successful grafting include the age of the donor cells. The results presented herein demonstrate that aged human cells may be used for transfection with transgenes for grafting.

ii. Choice and Construction of Vector

Although other vectors may be used, preferred vectors for use in the methods of the present invention are viral, including retroviral, vectors. The viral vector selected should meet the following criteria: 1) the vector must be able to infect the donor cells and thus viral vectors having an appropriate host range must be selected; 2) the transferred gene should be capable of persisting and being expressed in a cell for an extended period of time without causing cell death for stable maintenance and expression in the cell; and 3) the vector should do little, if any, damage to target cells. Murine retroviral vectors offer an efficient, useful, and presently the best-characterized means of introducing and expressing foreign genes efficiently in mammalian cells. These vectors have very broad host and cell type ranges, integrate by reasonably well understood mechanisms into random sites in the host genome, express genes stably and efficiently, and under most conditions do not kill or obviously damage their host cells.

Examples of retroviral vectors in which a single transgene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple transgenes. All of these vectors can transfer or incorporate a gene for a selectable marker so that transduced cells can be identified and generated. Because its characteristics are well-known and it stably expresses transgene product, MoMuLV is an especially desirable vector for use in delivering nerve growth factors into the brain according to the invention.

Construction of vectors for recombinant expression of nerve growth factors for use in the invention may be accomplished using conventional techniques which do not require detailed explanation to one of ordinary skill in the art. For review, however, those of ordinary skill may wish to consult Maniatis et al., in *Molecular Cloning: A Laboratory Manual,* Cold Spring Harbor Laboratory, N.Y. (1982). These methods are as applicable to construction of expression vectors for ex vivo grafting as they are to construction of such vectors for direct in vivo delivery.

Briefly, construction of recombinant expression vectors employs standard ligation techniques. For analysis to confirm correct sequences in vectors constructed, the ligation mixtures may be used to transform a host cell and successful transformants selected by antibiotic resistance where appropriate. Vectors from the transformants are prepared, analyzed by restriction and/or sequenced by, for example, the method of Messing, et al., (*Nucleic Acids Res.,* 9:309, 1981), the method of Maxam, et al., (*Methods in Enzymology,* 65:499, 1980), or other suitable methods which will be known to those skilled in the art. Size separation of cleaved fragments is performed using conventional gel electrophoresis as described, for example, by Maniatis, et al., (*Molecular Cloning,* pp. 133–134, 1982).

iii. Transgene Transformation of Donor Cells

Host cells may be transformed with expression vectors and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

Functional DNA transgenes may be inserted into donor cells by means other than vectors. For example, non-vector methods include nonviral physical transfection of DNA into cells; for example, microinjection (DePamphilis et al., *BioTechnique* 6:662–680 (1988)); electroporation (Tonequzzo et al., *Molec. Cell. Biol.* 6:703–706 (1986), Potter, *Anal. Biochem.* 174: 361–33 (1988)); chemically mediated transfection such as calcium phosphate transfection (Graham and van der EB, supra, Chen and Okayama, *Mol. Cell. Biol.* 7:2745–2752 (1987), Chen and Okayama, *BioTechnique,* 6:632–638 (1988)) and DEAE-dextran mediated transfer (McCutchan and Pagano, *J. Natl. Cancer Inst.* 41:351–357 (1968)); cationic liposomal mediated transfection (Felgner et al., *Proc. Natl. Acad. Sci. USA,* 84:7413–7417 (1987), Felgner and Holm, Focus 11:21–25 (1989) and Feigner et al., *Proc. West. Pharmacol. Soc.* 32:115–121 (1989)) and other methods known in the art.

The donor cells must be properly prepared for grafting. For example, for injection of genetically modified donor cells according to the present invention, cells such as fibroblasts obtained from skin samples are placed in a suitable culture medium for growth and maintenance of the cells, for example a solution containing fetal calf serum (FCS) and allowed to grow to confluency. The cells are loosened from the culture substrate for example using a buffered solution such as phosphate buffered saline (PBS) containing 0.05% trypsin and placed in a buffered solution such as PBS supplemented with 1 mg/ml of glucose; 0.1 mg/ml of $MgCl_2$; 0.1 mg/ml $CaCl_2$ (complete PBS) plus 5% serum to inactivate trypsin. The cells may be washed with PBS using centrifugation and are then resuspended in the complete PBS without trypsin and at a selected density for injection. In addition to PBS, any osmotically balanced solution which is physiologically compatible with the host subject may be used to suspend and inject the donor cells into the host.

The long-term survival of implanted cells may depend on effects of the viral infection on the cells, on cellular damage produced by the culture conditions, on the mechanics of cell implantation, or the establishment of adequate vascularization, and on the immune response of the host animal to the foreign cells or to the introduced gene product. The mammalian brain has traditionally been considered to be an immunologically privileged organ, but recent work has shown conclusively that immune responses can be demonstrated to foreign antigens in the rat brain. It is important to minimize the potential for rejection and graft-versus-host reaction induced by the grafted cells by using autologous cells wherever feasible, by the use of vectors that will not produce changes in cell surface antigens other than those associated with the phenotypic correction and possibly by the introduction of the cells during a phase of immune tolerance of the host animal, as in fetal life.

Issues of appropriate or faithful gene expression must be resolved to ensure that the level of gene expression is sufficient to achieve the desired phenotypic effect and not so high as to be toxic to the cell.

A problem associated with the use of genetically engineered cells as transplants for gene therapy is that as cells become quiescent (non-dividing) the expression of genes, including transgenes, has been observed to decrease ("down regulate") (Palmer et al., *Proc. Natl. Acad. Sci. USA* 88:1330–334 (1991)). Primary fibroblasts grafted into the brain do not continue to divide when implanted unless they are transformed and tumorigenic. They thus exist in a quiescent state in the brain. It is thus useful to provide means for maintaining and/or increasing expression of the transgene in the absence of cell division to promote long term stable expression of therapeutic genes used in fibroblasts for gene therapy.

Expression of a gene is controlled at the transcription, translation or post-translation levels. Transcription initiation is an early and critical event in gene expression. This depends on the promoter and enhancer sequences and is influenced by specific cellular factors that interact with these sequences. The transcriptional unit of many prokaryotic genes consists of the promoter and in some cases enhancer or regulator elements (Baneiji et al., *Cell* 27:299 (1981); Corden et al., *Science* 209:1406 (1980); and Breathnach and Chambon, *Ann. Rev. Biochem.* 50:349 (1981)). For retroviruses, control elements involved in the replication of the retroviral genome reside in the long terminal repeat (LTR) (Weiss et al., eds., In: The molecular biology of tumor viruses: RNA tumor viruses, Cold Spring Harbor Laboratory, Cold Spring Harbor, New York (1982)). Malawian murine leukemia virus (MLV) and Rous sarcoma virus (RSV) LTRs contain promoter and enhancer sequences (Jolly et al., *Nucleic Acids Res.* 11:1855 (1983); Capecchi et al., In: Enhancer and eukaryotic gene expression., Gulzman and Shenk, eds., pp. 101–102, Cold Spring Harbor Laboratories, Cold Spring Harbor, N.Y.).

Promoter and enhancer regions of a number of non-viral promoters have also been described (Schmidt et al., *Nature* 314:285 (1985); Rossi and de Crombrugghe, *Proc. Natl. Acad. Sci. USA* 84:5590–5594 (1987)). Methods for maintaining and increasing expression of transgenes in quiescent cells include the use of promoters including collagen type I ($\alpha$1 and $\alpha$2) (Prockop and Kivirikko, *N. Eng. J. Med.* 311:376(1984); Smith and Niles, *Biochem.* 19:1820 (1980); de Wet et al., *J. Biol. Chem.,* 258:14385 (1983)), SV40 and LTR promoters.

In addition to using viral and non-viral promoters to drive transgene expression in donor cells such as primary fibroblasts, an enhancer sequence may be used to increase the level of transgene expression. Enhancers can increase the transcriptional activity not only of their native gene but also of some foreign genes (Armelor, *Proc. Natl Acad. Sci. USA* 70:2702 (1973)). For example, in the present invention collagen enhancer sequences are used with the collagen promoter $\alpha$2(I) to increase transgene expression. In addition, the enhancer element found in SV40 viruses may be used to increase transgene expression. This enhancer sequence consists of a 72 base pair repeat as described by Gruss et al., *Proc. Natl. Acad. Sci. USA* 78: 943 (1981); Benoist and Chambon, *Nature* 290:304 (1981), and Fromm and Berg, *J. Mol. Appl. Genetics,* 1:457 (1982), all of which are incorporated by reference herein. This repeat sequence can increase the transcription of many different viral and cellular genes when it is present in series with various promoters (Moreau et al., *Nucleic Acids Res.* 9:6047 (1981).

Transgene expression may also be increased for long term stable expression after grafting using cytokines to modulate promoter activity. Several cytokines have been reported to modulate the expression of transgene from collagen $\alpha$2(I) and LTR promoters (Chua et al., connective Tissue Res., 25:161–170 (1990); Elias et al., Annals N.Y. Acad. Sci., 580:233–244 (1990)); Seliger et al., *J. Immunol.* 141:2138–2144 (1988) and Seliger et al., *J. Virology* 62:619–621 (1988)). For example, transforming growth factor (TFG)$\beta$, interleukin (IL)-1$\beta$, and interferon (INF)$\alpha$ or $\gamma$ down regulate the expression of transgenes driven by various promoters such as LTR. Tumor necrosis factor (TNF)$\alpha$ and TGF$\beta$1 up regulate and IL1$\beta$, may be used to control expression of transgenes driven by a promoter in donor cells such as fibroblasts. Other cytokines that may prove useful include basic fibroblast growth factor (bFGF) and epidermal growth factor (EGF).

Collagen promoter with the collagen enhancer sequence (Coil(E)) can also be used to take advantage of the high level of cytokines present in the brain following grafting of the modified donor cells to increase transgene expression. In addition, anti-inflammatory agents including steroids, for example dexamethasone, may be administered to the graft recipient immediately after implantation of the fibroblasts and continued, preferably, until the cytokine-mediated inflammatory response subsides. In certain cases, an immunosuppression agent such as cyclosporin may be administered to reduce the production of interferon-γ which down-regulates LTR promoter and Coll(E) promoter-enhancer, and reduces transgene expression.

For in vivo use, transgenes driven by collagen promoter are introduced into cells and then directly implanted into the brain without requiring further intervention. The cytokines released after grafting as part of the recipient's natural response will stimulate the collagen promoter driven transcription of the selected transgene.

Cytokines including the growth factors bFGF and EGF, may also be administered before, during or after grafting, to promote survival of grafted donor cells in the CNS.

In primates, transduced primary primate fibroblasts have been shown to express a human neurotrophin (hNGF) in vivo in the brain and CNS for up to 12 months, thereby providing a chronically available source for local NGF delivery to these tissues according to the invention.

C. Pharmaceutical Compositions for Use in the Invention

For delivery to a mammal, recombinant expression vectors may be placed into a pharmaceutically acceptable suspension, solution or emulsion. Suitable mediums include saline and liposomal preparations.

More specifically, pharmaceutically acceptable carriers may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Further, a composition of recombinant expression vectors may be lyophilized using means well known in the art, for subsequent reconstitution and use according to the invention.

In addition to the targeted vector delivery systems discussed supra, a colloidal dispersion system may also be used for targeted delivery. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome.

Liposomes are artificial membrane vesicles which are useful as delivery vehicles in vitro and in vivo. It has been shown that large unilamellar vesicles (LUV), which range in size from 0.2–4.0 μm can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes encoding the antisense polynucleotides at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques*, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distetroylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

D. Model for Loss of Motor Function Attributable to CST Damage

The animal model of dorsal hemisection lesions described in Example I demonstrates the efficacy of the inventive method. To produce the model, adult rats underwent bilateral dorsal column spinal cord lesions that remove the dorsal corticospinal projections, or underwent more extensive resections of the entire dorsal spinal cord bilaterally that remove corticospinal, rubrospinal, and cerulospinal projections. Animals underwent either limited lesions of the spinal dorsal columns, which contain 95% of the corticospinal projection or more extensive lesions (dorsal hemisection lesions) of the entire dorsal half of the spinal cord (containing corticospinal, rubrospinal, and cerulospinal projections together with some raphaespinal, propriospinal and vestibulospinal projections). Functional deficits were observed on a motor grid task requiring detailed integration of sensorimotor skills, with prolonged deficits occurring in the animals with more extensive injuries.

E. Treatment of Animals with Spinal Cord injuries Including Damage to CST Projections and Recovery of Motor Function in Animals Treated According to the Invention Methods for treatment of animals with spinal cord injuries including damage to CST projections according to the invention are described below. For convenience, the discussion refers to the neurotrophin administered according to the invention as NT-3; however, those of ordinary skill in the art will recognize that the methods described may be applied to other neurotrophins (e.g., NGF).

For direct treatment of cells in vivo, a pharmaceutical composition of a recombinant expression vector (described below) is injected into cells within the lesion or within diffusion distance of the lesion. Any puncture device suitable for use in delivering a drug into spinal tissue may be used to deliver the recombinant expression vectors of the invention. Expression of the vector is evaluated in vitro by biopsy of the lesion as described in Example II or by functional assessment of the clinical condition and motor skills of the treated animal.

The dosage of recombinant expression vector delivered using the method of the invention will vary depending on the desired response by the host and the vector used. Generally, it is expected that up to 100–200 μg of DNA or RNA can be administered in a single dosage, although a range of 0.5 mg/kg body weight to 50 mg/kg body weight will be suitable for most applications.

Using the described method, animals with dorsal hemisection lesions received grafts to the acute lesion site of autologous fibroblasts genetically modified to produce NT-3, or received non-modified fibroblasts to serve as control animals. Function was assessed one and three months later, and results were compared to functional findings in animals that received grafts of autologous fibroblasts genetically modified to secrete NGF. Animals were then sacrificed and responses of injured systems to NT-3-secreting and uninfected grafts were examined at the morphological level. Syngenic primary rat fibroblasts genetically modified to produce NT-3 were then grafted to acute spinal cord dorsal hemisection lesion cavities. Up to three months later, significant partial functional recovery occurred in NT-3 grafted animals together with a significant increase in corticospinal axon growth at and distal to the injury site.

Axonal growth occurred in the treated animals at distances of 8 mm caudal to the injury site, but not further, presumably corresponding to the distance that NT-3 diffused from grafts. Thus, each site of injury to CST projections in an injured animal (lesion) will preferably be contacted directly with NT-3 or an NT-3 secreting graft applied at intervals sufficient to allow NT-3 to diffuse onto the lesion i.e., the "diffusion distance" between the graft and at least the nearest edge of the lesion.

To this end, the 8 mm diffusion distance observed in rats can be extrapolated proportionately to smaller or longer spinal cord structures in other species and NT-3 delivered accordingly. In selecting sites for NT-3 delivery by syngenic cell grafting, it will be appreciated from the data in Example II that axonal growth may not extend into the graft itself. Therefore, depending on the extent of CST injury present, small grafts may be placed at shorter intervals or larger grafts placed at longer intervals to maximize, both contact of injured CST projections with secreted NT-3 and ungrafted surface area for axonal regrowth. In view of this disclosure, the performance of such calculations will be well within the level of ordinary skill in the art.

Intact ventral CST axons did not extend axons into the host gray matter, suggesting that injury to CST axons is a necessary event to induce responsiveness to NT-3. Developing corticospinal axons express the specific high-affinity NT-3 receptor trkC (Yee K T, O'Leary D. (1996) NT-3 and trkC expression patterns suggest their role in the development of corticospinal axon projections to the brainstem and spinal cord. Soc Neurosci Abstr 22:1468). Thus, although the invention is not intended to be limited by any particular theory as to its mechanism of action, specific activation of trkC receptors on injured CST axons likely accounts for the NT-3 responsiveness exemplified in this disclosure. Significantly, this finding also shows that uninjured spinal tissue will not be adversely affected by treatment of injured spinal tissue with NT-3, thereby enhancing the clinical safety of the inventive method.

Furthermore, NT-3 neurotrophic activity is apparently specific to injured CST projections to the exclusion of other injured regions of the spinal cord, thus allowing treatment to be targeted to CST projections. As shown in Example I, labeling to detect growth from axons in projections other than the corticospinal system demonstrated their non-responsiveness to cellularly-delivered NT-3. In particular, neurofilament and p75 immunolabeling showed no quantitative difference in axon penetration into NT-3-secreting and non-transduced fibroblast grafts. Similarly, specific labeling for serotonin (raphaespinal projections), TH and DBH (cerulospinal projections), CHAT (ventral horn motor and other axons), CGRP (dorsal root efferents), and substance-P (dorsal root c-fibers) showed no specific responses from these systems. Qualitative analysis of patterns of immunolabeling for these markers also failed to disclose specific alterations in growth patterns in the host spinal cord adjacent to the injury site when comparing NT-3-secreting with non-infected fibroblast grafts.

In contrast to earlier reports (see e.g., Xu X M, Guenard V, Kleitman N, Aebischer P, Bunge M B. (1995) A combination of BDNF and NT-3 promotes supraspinal axonal regeneration in Schwann cell grafts in adult rat thoracic spinal cord. Exp Neurol 134:261–272), NT-3 did not induce regenerative growth in vestibulospinal, reticulospinal and rubrospinal axons. Further, regenerative growth was not found in either neurons of the locus ceruleus or primary Ia sensory afferent projections. Specific immunolabels for several other supraspinal projections, including the rubrospinal, vestibulospinal and reticulospinal systems are not available, and the responses of these systems to cellularly-delivered NT-3 were therefore not determined in this experiment.

The invention having been fully described, its practice is further illustrated by the Examples set forth below. The examples do not limit the scope of the invention, which will be defined solely by appended claims.

Unless otherwise indicated, all abbreviations used in the Examples (e.g., "h" for hours, "ml" for milliliter, and so forth) shall have their art-accepted meanings. All references cited in the Examples are incorporated herein for the sole purpose of illustrating knowledge in the art concerning means for performing the specific tasks described.

EXAMPLE I

FUNCTIONAL EFFECTS OF CST LESIONS

Adult Fischer 344 rats weighing 160–200 gm were experimental subjects. Animals were housed three per cage and had free access to food and water except during periods of functional testing. Institutional guidelines for animal safety and comfort were adhered to.

A. Experimental Protocols

Functional consequences of spinal cord lesions were characterized in one group of the rats. Animals received limited mid-thoracic lesions of either the dorsal columns (containing caudally-projecting corticospinal axons and rostrally-projecting dorsal column sensory axons), or more extensive dorsal spinal cord hemisection lesions that interrupted multiple motor projections, including the corticospinal, rubrospinal, cerulospinal and some raphaespinal, vestibulospinal and propriospinal tracts.

More particularly, T7 dorsal laminectomies were performed on rats deeply anesthetized with a mixture (2 ml/kg) of ketamine (25 mg/ml), rompun (1.3 mg/ml), and acepromazine (0.25 mg/ml). The dura was opened and limited dorsal column (n=8) or more extensive bilateral dorsal hemisection lesions (n=7) were performed using a fine-tipped glass-pulled aspiration device. To make dorsal column lesions, the dorsal cord midline was identified and superficially incised with microscissors. The aspiration device with a 22 ga core diameter was then utilized to extend the lesion laterally to the lateral edges of the dorsal columns, and ventrally to the level of the CST where it lies just dorsal to the central gray matter and central spinal canal.

The CST was then aspirated fully at the 17 level; the transition from CST to dorsal portion of the central gray matter was readily identifiable as a distinct color change from white to gray matter. The last corticospinal fibers conspicuously adhered to the aspiration device tip and literally lifted away from the central gray matter, marking complete interruption of corticospinal fibers and arrival to a point immediately dorsal to the mid dorsoventral axis of the cord. The aspiration procedure was extended slightly more ventrally and laterally to ensure resection of all dorsal CST axons. Lesion extent was verified by complete interruption of anterograde transport of WGA-HRP injected into the hindlimb sensorimotor cortex and by examination of serial Nissl-stained sections.

To perform dorsal hemisection lesions, the dorsal columns and dorsal corticospinal tract were removed as indicated above. Using the dorsal column/corticospinal lesion as a guide for the desired dorsoventral depth of the lesion, the lesion was extended laterally to remove the lateral aspects of the cord bilaterally. Post-operatively, animals were kept warm, placed on beds of sawdust, received manual bladder evacuation for a period of approximately 10 days, and received IM-ampicillin (25 mg twice per day) to prevent and treat urinary tract infections. Animals regained automatic neurogenic bladder function after five to ten days.

B. Protocols for In Vivo Confirmation of CST Damage

Lesion completeness was verified by anterograde tracing of the CST and Nissl staining at the conclusion of functional testing. For anterograde tracing of the corticospinal projection, 300 nl of a 4% solution of wheat germ agglutinin-conjugated horseradish peroxidase (WGA-HRP; Sigma) were injected through pulled glass micropipettes (40 um internal diameter) into each of 12 sites spanning the rostrocaudal extent of the rat sensorimotor cortex (Paxinos, Watson, 1986) using a PicoSpritzer II (General Valve). Air-driven pulses of 15 nl per pulse, 20 pulses per site were delivered with a 2 sec latency between pulses. The micropipette tip remained in place for 30 sec prior to withdrawal. Animals were transcardially perfused 48 hr later with 1% paraformaldehyde/1.25% glutaraldehyde followed by 10% buffered sucrose. 35-um-thick sections were cut in the sagittal plane and divided into series of six sections. Three of every six sections were reacted with a modification of the TMB method of Mesulam (Mesulam, 1978), and the remaining sections were Nissl-stained. TMB-reacted sections were viewed using a darkfield condenser attached to a Olympus BM-1 microscope. Lesion completeness in animals that underwent dorsal column lesions was verified by complete interruption of WGA-HRP transport in TMB-reacted sections and by loss of all dorsal column white matter on Nissl-stained sections. Lesion completeness in animals that underwent dorsal hemisection lesions was similarly determined by loss of all WGA-HRP transport and by loss of dorsal spinal cord white and gray matter on Nissl-stained sections visualized in the coronal plane.

Assessment of lesion completeness by WGA-HRP labeling and Nissl staining indicated complete interruption of corticospinal pathways in 7 of 8 animals that underwent dorsal column lesions and all animals that underwent dorsal hemisection lesions. The single animal with an incomplete lesion was not included in analysis of functional outcomes.

C. Functional Testing Protocols

One month after surgery, and again two months later, functional capabilities in lesioned animals were compared to unlesioned animals, in two groups of eight animals. Functional performance was examined using art accepted functional tests based on methods reported by Goldberger M E, Bregman B S, Vierck J R, Brown M. (1990) Criteria for assessing recovery of function after spinal cord injury: behavioral methods. Exp Neurol 107:113–117; and Kurnkel-Bagden E, Dai H N, Bregman B S. (1993) Methods to assess the development and recovery of locomotor function after spinal cord injury in rats. Exp Neurol 119:153–164, the disclosures of which are incorporated herein for the sole purpose of providing sources for further reading for those of skill in the art.

The functional tests involved three tasks:

1) conditioned locomotion over a grid (grid task), testing the ability of the rat to perform sensorimotor integration to avoid making "footfall" errors through the grid, a test that partially reflects function of supraspinal motor projections to the spinal cord; 2) conditioned locomotion over a flat runway with detailed footprint analysis (base of support, angle of footpad rotation, and stride length), a task that reflects the integrity of both supraspinal motor projections to the cord and segmental (local) spinal reflex motor skills; and 3) ability and time to climb onto an elevated platform, a task that reflects in part connections between forelimb and hindlimb motor systems (propriospinal pathways).

Of these three tasks, the grid task is putatively the most sensitive to sensorimotor integration performance, since rats can walk on a stationary surface (task 2) or climb onto a platform (task 3) without the degree of sensory feedback and motor coordination that is required to accurately sense the location of a narrow grid bar, grasp the bar with the limbs, and ambulate forward (task 1).

More specifically, the tests performed entailed the following:

1) Grid locomotion (wire grid task): Animals were required to navigate across a 150 cm plastic grid runway containing 40×40 mm holes to reach a food reward, after prior food deprivation for 48 hours (no more than 10–15% loss of body weight). After five days of pretraining on the grid, subjects underwent five more days of testing, four trials per day. Footfalls (failure to grasp a rung resulting in drop of the foot below the plane of the grid) made while crossing the grid on the last day of testing were quantified using video monitoring. Data were presented as number of footfalls to cross the platform averaged across the four trials on the final day of testing. 2) Platform locomotion with footprint analysis: Animals were placed on an 8-cm-wide by 8-foot-long platform with a food reward at the end. Over five days of training on the runway, rats learned to walk toward the food reward, thereby producing continuous locomotion. Animals were tested for 5 additional days after inking the hind paws (left blue, right red) and ambulating on white paper Each footprint consisted of the paired footprint pads with 5 toe prints. A total of 10 footprint pairs were examined from the final day of testing, using sets of footprints containing at least 3 consecutive strides. The following measurements were made: a) stride length, the distance between foot pads on two consecutive footprints; b) base of support, distance between right and left foot; and c) angle of rotation, the angle of intersection between lines defined by the angle of the footpad and toes, drawn according to standardized criteria (Kunkel-Bagden et al., 1993). Ten samples from each subject were analyzed, and individual subject means were determined. 3) Elevated platform task: The subject's forelimbs were placed on a Velcro pad of a platform located 18 inches above ground level. The latency to climb onto the top of the platform was measured. Intact subjects normally climb onto the platform with less than a one second latency, using their hindlimbs to assist the climb onto the platform. After five days of pretesting (three trials/day), latencies were quantified from three additional trials per day conducted over a 3-day period. Results from the 9 total trials were averaged and compared.

Comparisons between groups were made using ANOVA statistical analysis with post-hoc Fisher's least square difference.

D. Results of Functional Tests

Figure 1B:
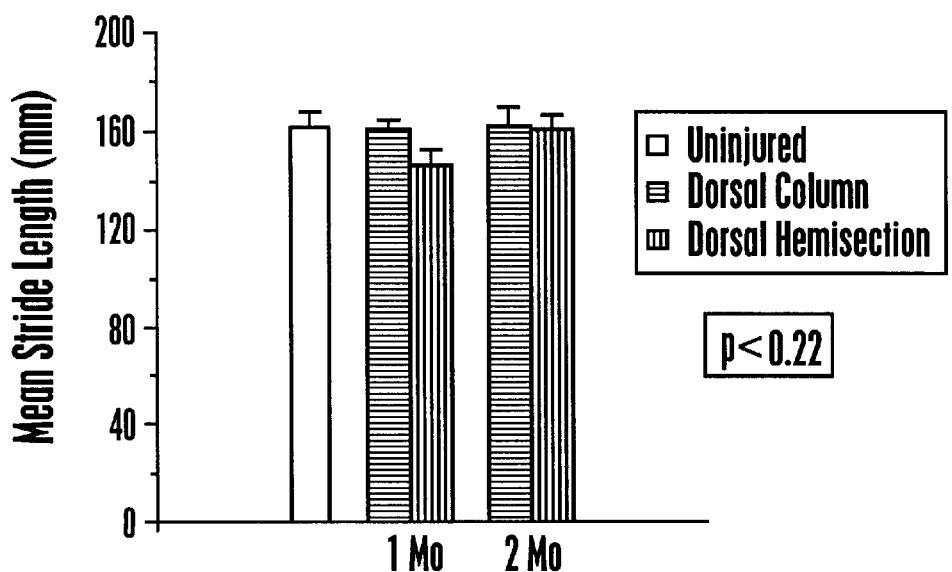
FIGS. 1b–d: Platform locomotion: Rats with dorsal hemisection lesions and dorsal column lesions do not show significant deficits in stride length (b; Anova $p=0.22$), base of support (c; Anova $p=0.18$), or angle of rotation (d; Anova $p=0.072$).
Figure 1C:
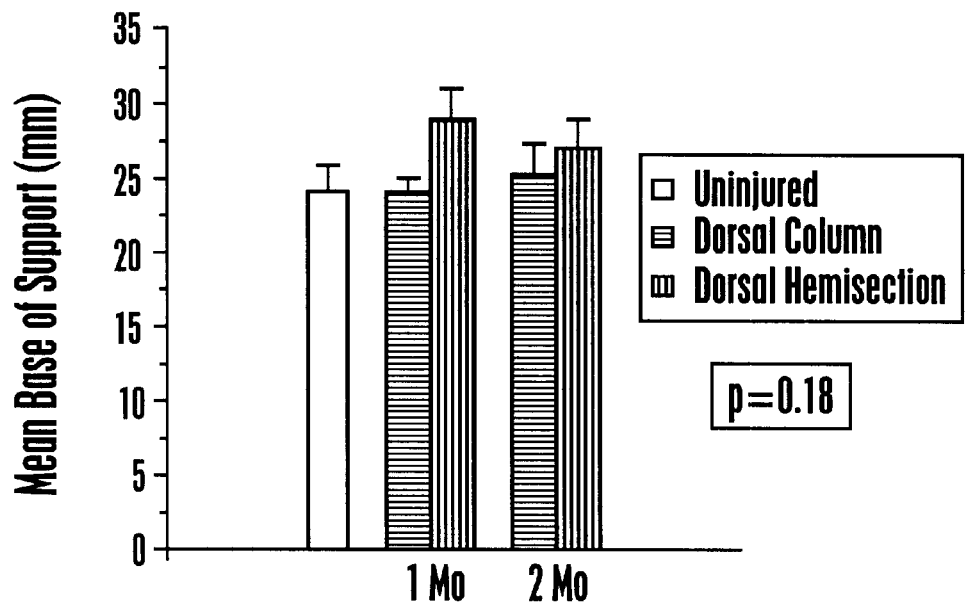
Figure 1D:
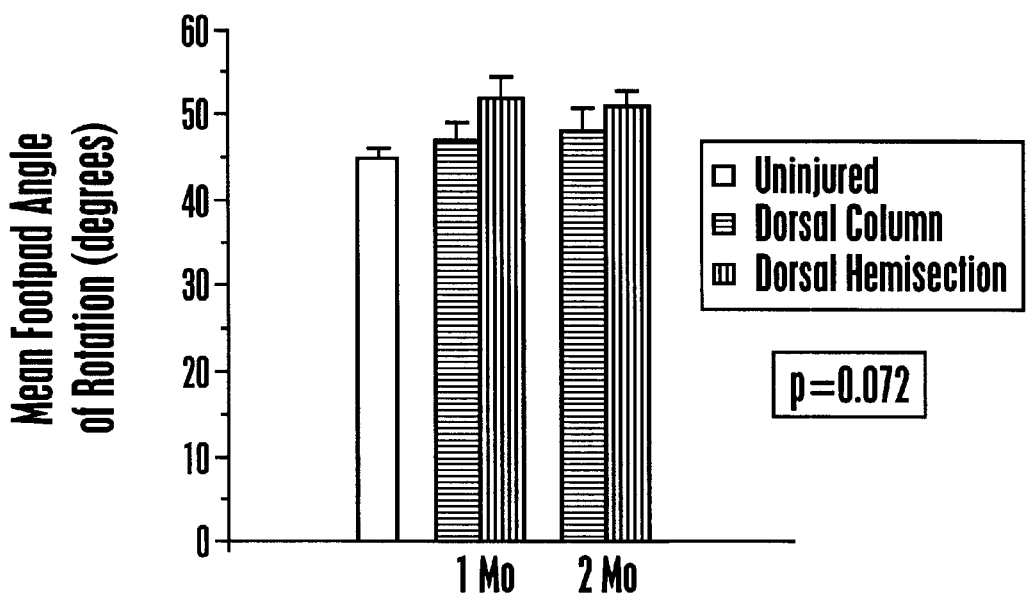

Deficits lasting for at least two months were found on the grid task in animals that received dorsal hemisection lesions (FIG. 1a). Functional deficits did not occur on runway locomotion tasks in either lesioned group (FIGS. 1b–d), nor on the elevated platform task (mean latency=1.1±0.3 sec in intact animals, 1.2±0.2 see in animals with dorsal column lesions, and 1.2±0.1 sec in animals with dorsal hemisection lesions, p=0.74). However, the task that most sensitively assesses sensorimotor integration, the grid locomotion task, shows long-term disruption after dorsal hemisection lesions.

EXAMPLE II

EFFECTS OF CELLULARLY DELIVERED NT-3 ON THE LESIONED SPINAL CORD

A. Treatment Protocol

Results of the preceding experiment indicate that combined lesions of several dorsal spinal cord motor systems can cause specific long-lasting sensorimotor functional deficits. This experiment was designed to examine the effects of a putative spinal cord neurotrophic factor, NT-3, on morphology and function following a spinal cord injury involving the CST.

To this end, adult rats underwent dorsal hemisection lesions as described in Example I. Experimental subjects then received grafts to the acute lesion cavity of syngenic fibroblasts genetically modified to produce NT-3 (n=21). Control subjects received either grafts of primary non-transduced fibroblasts (n=22 animals) or grafts of NGF-producing fibroblasts (n=8), a neurotrophic factor that promotes robust growth of i) primary spinal afferent sensory systems of the dorsolateral fasciculus, ii) cerulospinal axons, and iii) ventral horn motor axons. The NGF group served as a control group of subjects that received a neurotrophin other than NT-3.

Specifically, primary syngenic Fischer 344 rat fibroblasts were genetically modified to produce and secrete human NT-3. The 908-bp coding sequence for human NT-3 was inserted in a Moloney leukemia virus retroviral vector lacking the gag, pol and env genes, and 10–15 ug of plasmid DNA was transfected into the PA317 amphotropic producer cell line (packaging line) by lipofection. Conditioned medium from these cultures was used to infect primary fibroblasts. In vitro production of human NT-3 mRNA was verified by Northern blot, and production of biologically active protein was verified by a significant increase in numbers of the TH-immunolabeled neurons in cultures of E14 fetal anterior rhombencephalon by conditioned medium (CM) from cultures of NT-3 transfected cells compared to CM from control-transfected cells (p<0.05).

Control fibroblasts were not genetically modified; these cells were used in grafts in control-lesioned subjects. Thus, cells in control subjects differed from NT-3 transfected cells by only a single set of genes. $2.5 \times 10^6$ transduced fibroblasts (NT-3 or control) were suspended into 2 ml of a chilled liquid solution of Type I rat tail collagen (Sigma). After incubation for 48 hr at 37° C., the collagen/cell mixture was cut into small pieces and grafted into in vivo T7 spinal cord dorsal hemisection lesion cavities in adult Fischer 344 rats (n=21). Control subjects received either: a) grafts of primary non-transduced fibroblasts (n=22 animals), b) lesions alone without grafts (n=6), or c) grafts of NGF-producing fibroblasts.

One month and three months post-operatively, rats underwent functional testing on the grid task, platform task with footprint analysis, and elevated platform. At the completion of functional testing, animals were sacrificed and examined for growth responses in the injured region. Lesion completeness was determined on Nissl-stained sections and anterograde WGA-HRP labeling. Growth of the lesioned CST was determined by examining and quantifying WGA-HRP labeling in ten NT-3-grafted and 15 uninfected fibroblast control grafted animals. Growth responses from serotonergic, cerulospinal, and local motor systems were determined by immunolabeling (in eight NT-3-grafted and eight uninfected fibroblast control grafted animals).

B. In Vitro Testing Protocols

Anterograde Labeling of CST Projections and Quantification of CST Regrowth:

The methods used to inject WGA-HRP for anterograde labeling of CST projections are described in Example I. To measure the amount of CST growth in lesioned subjects, WGA-HRP granules were quantified using NIH Image software. Measurements were controlled for differences in efficiency of WGA-HRP labeling between animals (see below). Labeling was performed in 10 NT-3-grafted animals and 15 control-lesioned animals by quantifying the density of WGA-HRP reaction product under dark field illumination at the level of the lesioned corticospinal tract (0 mm), and 4, 8 and 12 mm distal to the most caudal aspect of the lesioned CST. Any labeling artifact was edited out of sections prior to quantification.

The number of pixels occupied by reaction product in every labeled section was quantified using NIH Image software on a video image of each 100× magnified section transmitted by a high-resolution Sony CCD camera. Thresholding values were chosen that maximized contrast between reaction product and background, and were held constant between all subjects. A fixed box size of 552×436 pixels at 100× magnification corresponding to a sample area of 0.24 mm$^2$ was used to sample each subject. Total labeled pixels at each distance from the lesioned CST were quantified in every HRP-labeled section (every 9-of-10 sagittal-sectioned sections per animal) to generate the total density of sprouted CST fibers at each distance from the transected CST. To correct for differences in HRP labeling efficiency between animals, a baseline labeling density measurement (BLDM) was established.

To determine the BLDM, the density of the labeled CST was measured at a point 1.5 cm rostral to the lesion site in each subject. Then the pixel values at each level (0, 4, 8, 12 mm distal to corticospinal lesion) were divided by the animal's own BLDM compensation factor. These corrected values were then compared between animals to determine a specific and direct measurement of CST growth. The presence of significant differences in growth among groups was determined by ANOVA.

Immunolabeling:

Animals were transcardially perfused with 100 ml cold 0.1 M phosphate-buffered saline (PBS) followed by 300 ml 4% paraformaldehyde in PBS. Spinal cords were removed, post fixed overnight in 4% paraformaldehyde in PBS, and then left for three days in phosphate buffer containing 30% sucrose at 4° C. Sagittal sections were cut at 35 um intervals with a cryostat. Every sixth section was immediately mounted on glass slides for Nissl staining. Remaining alternate sections were processed for immunocytochemical labels for the low-affinity p75 NGF receptor (monoclonal IgG-192 antibody at 1:100 dilution, gift of Dr. C. E. Chandler), neurofilament (NF; RT97 monoclonal antibody from Boehringer Mannheim against 200 kD NF at 1:250 dilution), choline acetyltransferase (ChAT, for cholinergic fibers; polyclonal rabbit antibody at 1:5000 dilution, gift of Dr. L. G. Hersh), tyrosine hydroxylase (TH, for dopaminergic and noradrenergic fibers; monoclonal antibody from IncStar Corp. at 1:1000 dilution), dopamine beta hydroxylase (DBH, for noradrenergic fibers; polyclonal rabbit antibody from Eugene Tech at 1:3000 dilution), serotonin (5-HT; polyclonal rabbit antibody from Eugene Tech at 1:1000 dilution), calcitonin gene-related peptide (CGRP, for sensory fibers; polyclonal rabbit antibody from Chemicon at 1:8000 dilution) and glial fibrillary acidic protein (GFAP; monoclonal antibody from Boehringer Mannheim at 1:250 dilution).

All immunocytochemical labeling was performed by 1) incubating free-floating sections for 24 hr in primary antibody solution in 0.1M Tris-saline containing 1% blocking serum and 0.25% Triton X-100; 2) incubation for one hour with biotinylated goat anti-rabbit IgG (for polyclonal antibodies) or biotinylated horse anti-mouse IgG (for monoclonal antibodies; Vector Laboratories) diluted 1:200 with Tris-saline containing 1% blocking serum; 3) one hour incubation with avidin-biotinylated peroxidase complex (Vector Elite™ Kit) diluted 1:1000 with Tris-saline containing 1% blocking serum; and 4) treatment for 3–15 minutes with 0.05% solution of 3.3' diaminobenzidine, 0.01% $H_2O_2$, and 0.04% nickel chloride in 0.1M Tris-buffer. Immunolabeled tissue sections were mounted onto gelatin-coated glass slides, air-dried, dehydrated and covered with Permount and glass coverslips. Sections were examined microscopically for graft survival and lesion extent. Immunolabeled sections were examined to determine the phenotype and extent of fiber penetration within grafts.

Double Label Immunofluorescence Confocal Microscopy:

To identify the nature of host/graft interactions that might influence axonal penetration into the intraspinal cell grafts, double-labeling for neurofilament (NF) and glial fibrillary acid protein (GFAP) was performed in four animals (two NT-3 and two uninfected fibroblast control grafts). Subjects were perfused with 4% paraformaldehyde in 0.1M phosphate buffer (PB). Spinal cords were removed and serially sectioned in the sagittal plane on a cryostat at 35 um intervals. Sections were rinsed 3x-10 min each in TBS (0.1M). Sections were incubated in TBS+5% normal horse serum+0.25% Triton-X for 1 hr, then transferred into the first primary antibody directed against neurofilaments (NF; monoclonal RT97 antibody at 1:175 dilution [Boehringer-Mannheim]) and incubated overnight at 4° C. on a rotating platform. The following day, sections were rinsed 3x10 min. each in TBS+0.25% Triton-X, then incubated in horse anti-mouse biotinylated secondary (Jackson Immunochemicals, 1:200) for 2.5 hr. Sections were then rinsed 3x in TBS and incubated in DTAF-streptavidin as a tertiary (Jackson Immunochemicals, 1:300) for an additional 2.5 hr. Sections were rinsed again in TBS, then blocked in TBS+5% normal donkey serum for 1 hr. Sections were then incubated in the second primary, glial fibrillary acidic protein (GFAP, polyclonal, 1:750, DAKO) overnight at 4° C. The following day, sections were incubated in secondary donkey anti-rabbit-Texas Red (Jackson Immunochemicals, 1:200) for 2.5 hr, then rinsed. Double-immunolabeled sections were mounted onto glass slides and coverslipped with FluoroMount-G™ (Southern Biotechnology Assoc.) and observed using absorption spectra filters of bandpass 490 (DTAF) and 545 (rhodamine). Sections were observed and imaged using a Bio-Rad MRC-1024 confocal microscope to examine the association of reactive glial processes to neuritic patterns of labeling.

In vivo transgene expression:

The ability of grafts of human NT-3-expressing cells to maintain transgene expression over time in vivo was assessed in separate animals by performing rt-PCR on fresh dissections of NT-3-producing cell grafts to non-lesioned spinal cords. RNA was isolated from fresh cord using the method of Chomczynski and Sacchi (Chomczynski, Sacchi, 1987). 1 ug total RNA was reverse transcribed according to manufacturer's instructions (Boehringer Mannheim, Germany) using random primers. The 50 ul PCR reaction contained ¹⁄₁₀ first strand synthesis, 0.5 ug of each primer, 1.5 mM $MgCl_2$, 50 mM $MgCl_2$, 50 mM KCl, 10 mM Tris-HCl pH 9.0, 0.1% Triton X-100, 0.2 mM DNTP, 2.5 U Taq Polymerase (Promega, Wis.) and amplification was carried out for 35 cycles (60s at 94°; 30s at 60° C; 60s at 72° C). Sequences of primers are published elsewhere (Senut M-C, Tuszynski M H, Raymon H K, et al. (1995) Regional differences in responsiveness of adult CNS axons to grafts of cells expressing human neurotrophin-3. Exp Neurol 135:36–55). 10 ul of each PCR reaction were separated in a 2% agarose gel. Grafts in two animals each were tested a time points of two wk, one mo, and three mo, and two additional animals were sampled at six mo to gauge the extent of prolonged in vivo transgene expression. Expression was obtained throughout the test period.

Statistics:

Differences in quantitative variables between groups were tested by analysis of variance. Post-hoc differences were assessed Fisher's LSD. For all data collection, experimenters were blinded to group identities.

C. In Vivo Testing Protocols

Functional tests on treated and control rats were performed as described in Example I.

D. Treatment Results

Figure 2:
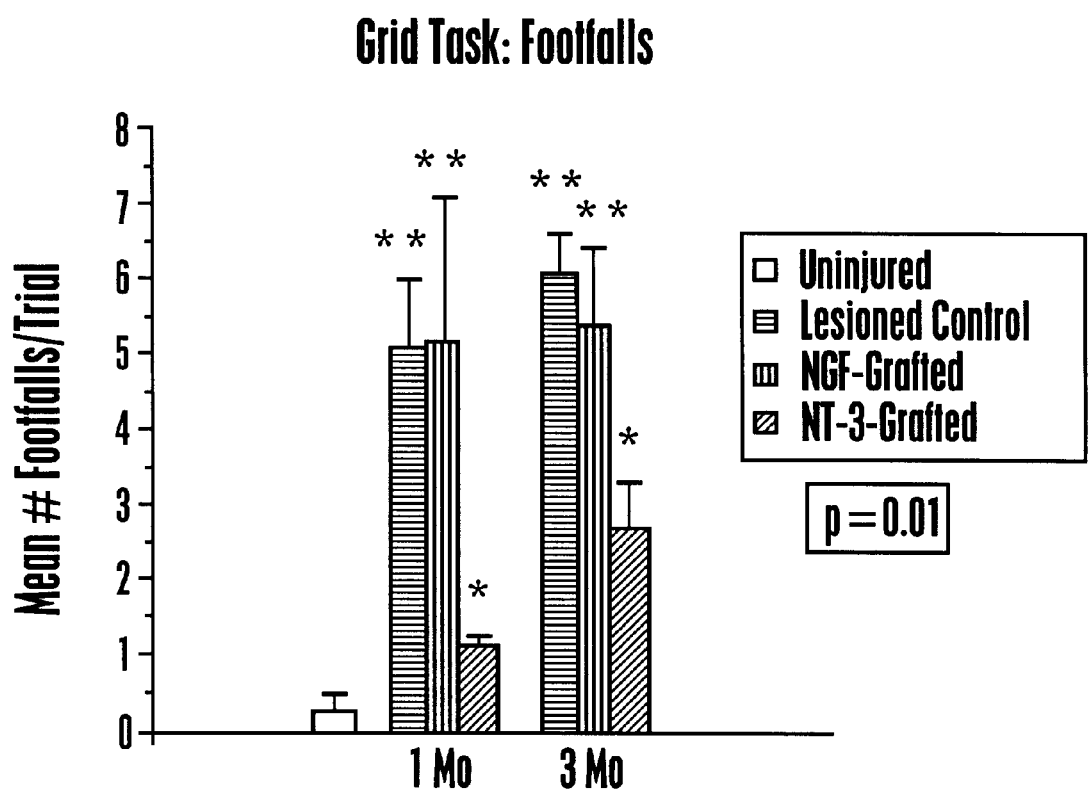
FIG. 2: Functional recovery in recipients of NT-3-secreting grafts. Functional recovery in NT-3 grafted subjects is observed on the grid task compared to control-grafted and NGF-grafted subjects (Anova, $p=0.01$). NT-3 grafted subjects perform significantly better than control- and NGF-grafted subjects at 1 and 3 months post-grafting (post-hoc Fischer's), but NT-3 subjects also differ significantly from intact subjects. ** indicates significant difference from NT-3-grafted and uninjured animals; * indicates significant difference from uninjured animals. Comparison of degree of recovery in NT-3 subjects at 1 and 3 months post-lesion shows no significant difference (post-hoc Fischer's). Functional testing results were replicated in two separate series of experiments.
Figure 3A:
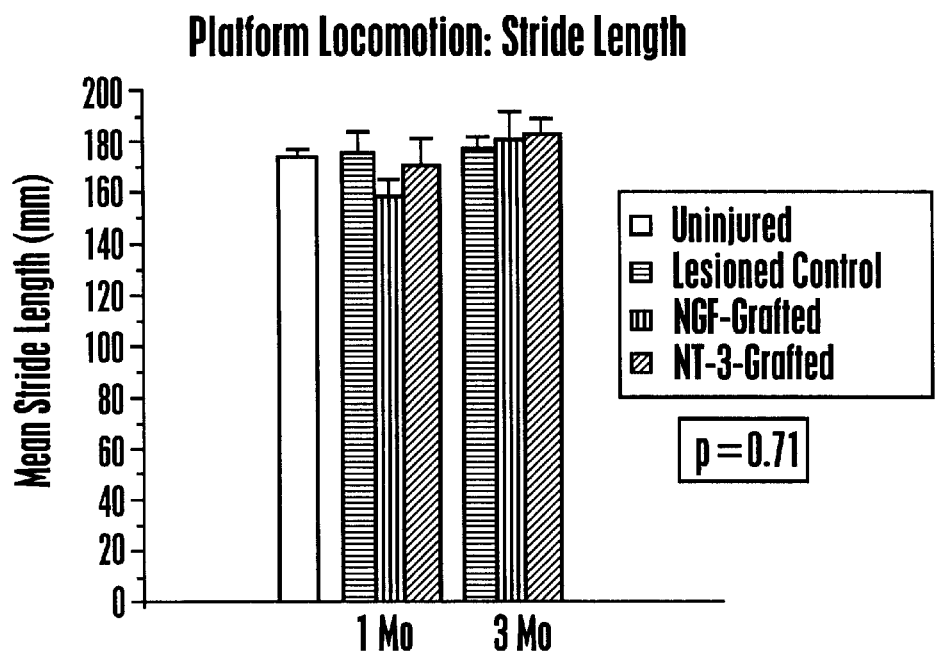
FIG. 3 (*a* through *c*): Function on tasks unaffected by dorsal hemisection lesions: Platform locomotion (*a–c*) is unaffected by the experimental manipulations, indicating that grafts do not alter function on these tasks.
Figure 3B:
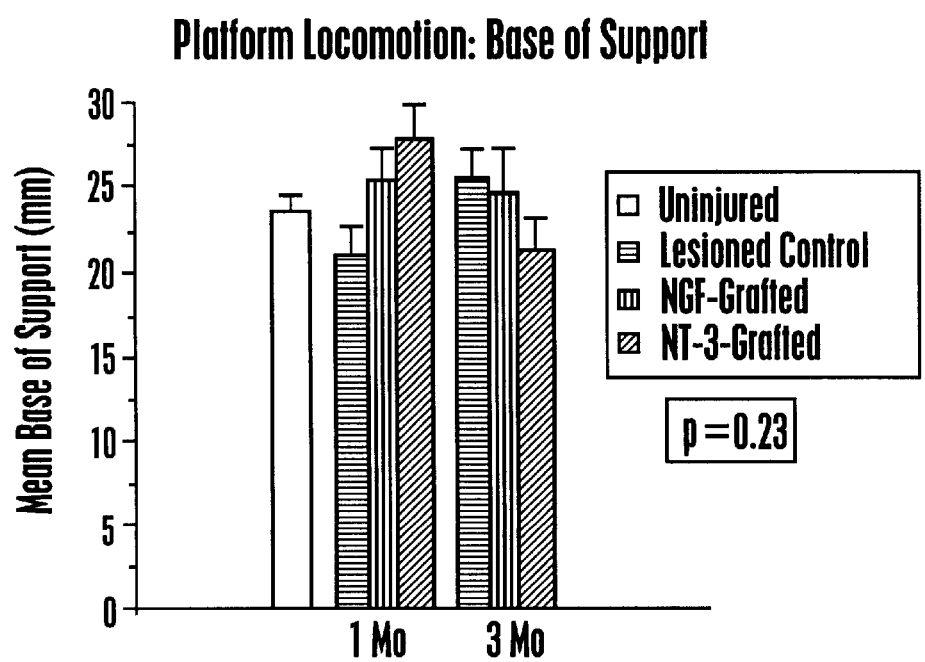
Figure 3C:
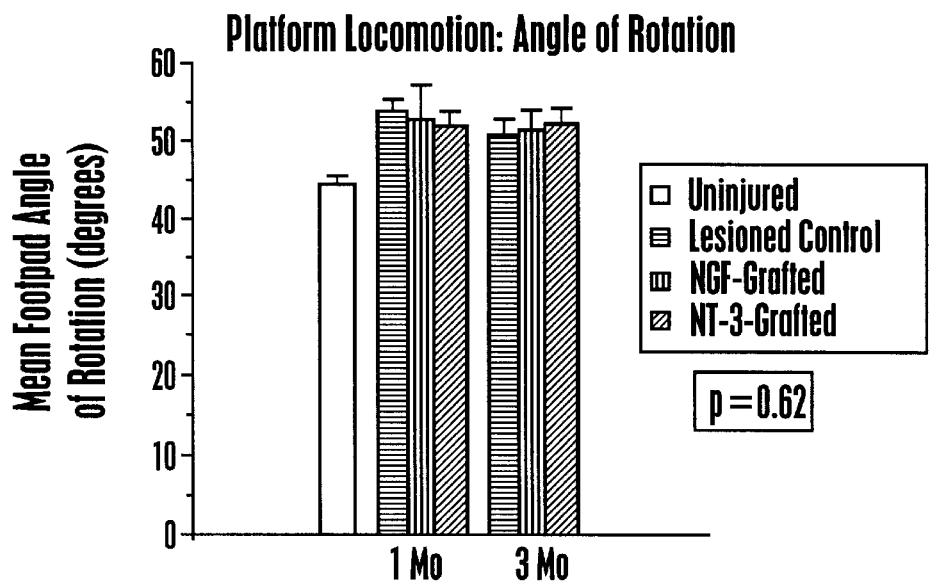
Figure 4:
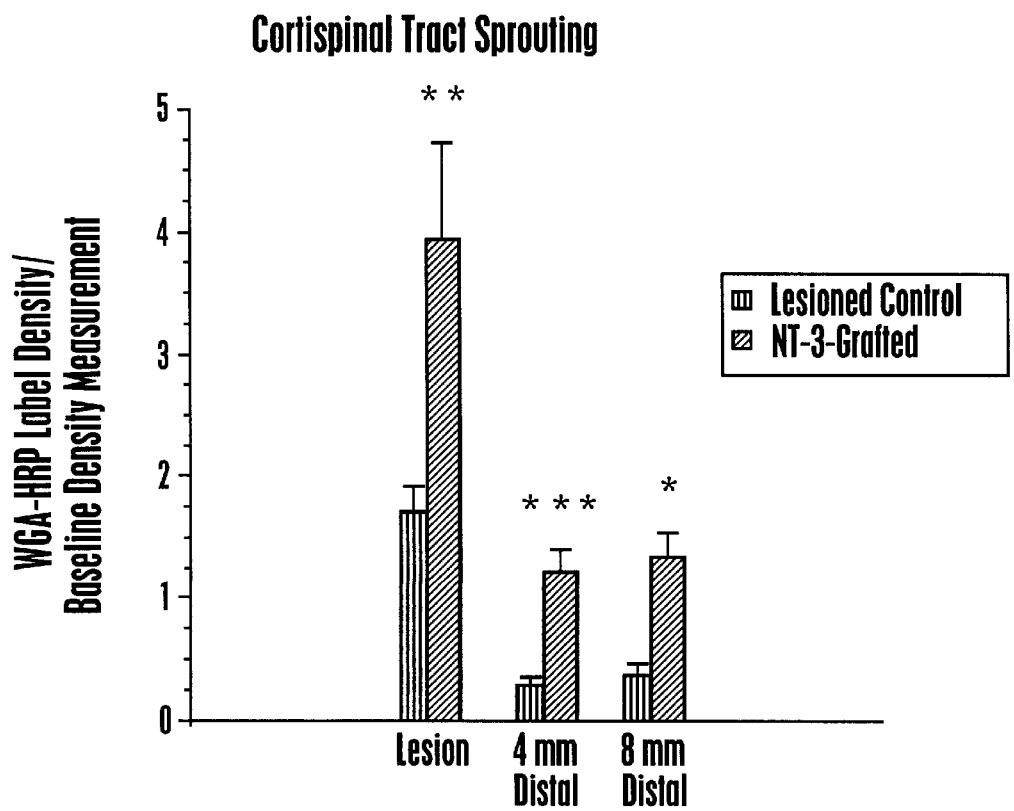
FIG. 4: Quantification of corticospinal axon growth. A significant increase in corticospinal axon growth is evident in NT-3 grafted subjects compared to control uninfected fibroblast grafted animals at the lesion site, 4 mm distal to the lesion, and 8 mm distal to the lesion. Differences are not significant 12 mm caudal to the lesion site. *, $p<0.05$; , $p<0.01$; *, $p<0.005$.

Function:

On functional testing, recipients of NT-3-secreting grafts showed significant recovery on the grid task compared to uninfected fibroblast control graft recipients (FIG. 2) at one and three months post-grafting (p<0.01). Recipients of NGF-secreting grafts did not show functional recovery (FIG. 2), indicating the specificity of the functional effect to recipients of NT-3-secreting cell grafts. NT-3 graft recipients performed significantly better than the other lesioned groups on the grid task, but also differed significantly from intact animals. As observed in the first set of experiments above, deficits on platform motor tasks that did not require extensive sensorimotor integration were not detected, nor did NT-3 grafts impair these functions (FIG. 3). Similarly, deficits were not present on the elevated platform task (data not shown).

Histology:

Findings were investigated in all NT-3 and control-grafted animals (findings in NGF-grafted animals have been previously reported, and are not repeated here (Tuszynski M H, Peterson D A, Ray J, Baird A, Nakahara Y, Gage F H. (1994) Fibroblasts genetically modified to produce nerve growth factor induce robust neuritic ingrowth after grafting to the spinal cord. Exp Neurol 126:1–14; and Tuszynski M H, Gabriel K, Gage F H, Suhr S, Meyer S, Rosetti A. (1996) Nerve growth factor delivery by gene transfer induces differential outgrowth of sensory, motor and noradrenergic neurites after adult spinal cord injury. Exp Neurol 137:157–173)). Grafts of NT-3-secreting and control uninfected fibroblasts survived in the lesion cavity through the three month grafting period. WGA-HRP labeling of the injured corticospinal projection demonstrated significant growth of CST axons in recipients of NT-3-secreting grafts at, and distal to, the spinal cord lesion site compared to control animals. Growth was significant for up to 8 mm distal to the lesion site. A statistically significant increase in growth beyond this point, at 12 mm, was not observed.

Of note, corticospinal axons extended through spinal cord gray matter but not into white matter tracts. Further, only the lesioned dorsal CST appeared to extend axons in response to the presence of the NT-3-secreting graft, whereas an enhancement in sprouting of the unlesioned ventral CST was not observed. The latter finding was evident in two ways: first, WGA-HRP labeled axons of the ventral CST were not observed to traverse the ventral white to gray matter interface, whereas numerous axons crossed the interface between the dorsal CST and gray matter. Second, the number of WGA-HRP labeled axons in the ventral CST did not differ between NT-3-grafted and control uninfected fibroblast-grafted subjects: 5.9±1.5 axons per section were labeled in the ventral CST in NT-3-grafted subjects compared to 5.1±1.2 axons per section in control-lesioned subjects (p=0.83). Thus, axons of the lesioned dorsal CST rather than axons of the intact ventral CST responded to NT-3-secreting grafts, and contributions of the CST to functional recovery, if any, were likely derived from the dorsal rather than ventral CST.

In some cases, WGA-HRP labeling revealed distinct growth from the tips of lesioned CST axons at the injury site to points distal, representing regeneration of injured axons. In other cases, WGA-HRP labeling that occurred at and distal to the injury site was punctate in nature and could represent either regeneration or sprouting of axons near the injury site.

Axonal/glial associations:

In no case did corticospinal axons penetrate NT-3-secreting or control grafts. This lack of CST penetration into grafts could result either from glial/inflammatory responses at the host/graft interface that blocked growing axons, or to components of the graft substrate that were non-permissive for axon growth. To address the association of spinal cord axons with glia at the lesion site and at the host/graft interface, sections double-labeled for NF and GFAP were examined. At the host/graft interface, significant upregulation of GFAP expression was observed; however, several NF-labeled processes readily penetrated regions of GFAP upregulation to pass through the glial "barrier" and directly penetrate both NT-3-secreting and control grafts. Indeed, both NF-IR and GFAP-IR processes continued to penetrate grafts for some distance, and NF- and GFAP-IR processes were often co-associated within grafts. In other instances, NF-IR processes penetrated grafts without specific co-association with GFAP-IR processes. The overall nature of the astroglial response did not differ between NT-3 and control graft recipients. Thus, glial responses at the host/graft interface did not present an impenetrable wall to lesioned axons; on the contrary, in some instances astrocytic processes were intimately co-associated with penetrating axons.

Responses of other axonal phenotypes to NT-3-secreting cell grafts:

Immunolabeling revealed penetration of some axonal phenotypes into both NT-3-secreting and control grafts, but no significant augmentation of this growth in NT-3-secreting graft recipients. NF immunolabeling revealed modest axonal growth into both graft types. Specific labeling to identify the transmitter phenotype of penetrating axons indicated that most originated from primary sensory afferents, evidenced by immunolabeling for CGRP and Substance P, with occasional responses from 5-HT, TH- and DBH-labeled axons. No significant sprouting responses were observed from ChAT immunolabeled axons into either NT-3 or control grafts. Alterations in immunolabeling patterns of these markers in host regions surrounding the graft were not observed, in distinction to the specific augmentation in growth of WGA-HRP labeled CST axons in NT-3-graft recipients. There were no differences in axonal growth within the host cord when comparing lesioned, non-grafted animals and lesioned, fibroblast-grafted animals.

In vivo expression of the human NT-3 transgene:

For the three-month period of this experiment, and indeed for at least 6 mo in vivo, transgene expression was verified by rt-PCR performed on fresh grafts placed in unlesioned rat spinal cords.

The invention having been fully described, those of ordinary skill in the art may recognize modifications and extensions to the invention. All such modifications and extensions are considered to be within the scope of the invention.

What is claimed is:

1. A method for treating a spinal cord injury involving a lesion of the corticospinal tract ("CST") in a host, comprising administering a CST neurotrophin to the lesion, whereby administration is made by introducing a recombinant expression vector encoding the CST neurotrophin within diffusion distance of the lesion, such that expressed CST neurotrophin induces growth of corticospinal axons, and restores a degree of motor function, which motor function was lost as a consequence of the spinal cord injury, to the host.

2. The method according to claim 1 wherein the CST neurotrophin is NT-3.

3. The method according to claim 1 wherein the CST neurotrophin is βNGF.

4. The method according to claim 1, wherein the recombinant expression vector is further introduced into cells at the site of the lesion.

5. A method for treating a spinal cord injury involving a lesion of the corticospinal tract ("CST") in a host, comprising administering a CST neurotrophin to the lesion, whereby administration is made by introducing cells transfected with a recombinant expression vector encoding the CST neurotrophin within diffusion distance of the lesion, such that expressed CST induces growth of corticospinal axons, and restores a degree of motor function, which motor function was lost as a consequence of the spinal cord injury, to the host.

6. The method according to claim 4 wherein the transfected cells are fibroblasts.

7. The method according to claim 4 wherein the CST neurotrophin is NT-3.

8. The method according to claim 4 wherein the CST neurotrophin is βNGF.

9. The method according to claim 4 wherein the CST neurotrophin is leukaemia inhibitory factor.

10. The method according to claim 4 wherein the cells transfected with the recombinant expression vector encoding a CST neurotrophin are grafted within diffusion distance of the lesion.

11. The method according to claim 5, wherein the cell grafts are further made at the site of the lesion.

* * * * *

UNITED STATES PATENT AND TRADEMARK OFFICE
CERTIFICATE OF CORRECTION

PATENT NO.   : 6,167,888 B1
DATED        : January 2, 2001
INVENTOR(S)  : Mark H. Tuszynski, Ray Grill and Fred H. Gage It is certified that error appears in the above-identified patent and that said Letters Patent is hereby corrected as shown below:

Column 3,
Line 19, delete "(SEQ.ID.No. 1)"
Line 21, delete "(SEQ.ID.No. 2)"
Line 54, after "secrete" delete ":".

Signed and Sealed this

Sixth Day of July, 2004

JON W. DUDAS
*Acting Director of the United States Patent and Trademark Office*